United States Patent [19]

Sandhu

[11] Patent Number: 4,492,107
[45] Date of Patent: Jan. 8, 1985

[54] ACOUSTIC POWER METER

[75] Inventor: Jaswinder S. Sandhu, Chicago, Ill.

[73] Assignee: RAJ Technology Partnership, Chicago, Ill.

[21] Appl. No.: 360,623

[22] Filed: Mar. 22, 1982

[51] Int. Cl.$^3$ ............................................. G01H 9/00
[52] U.S. Cl. ................................ 73/1 DV; 73/570; 73/603; 350/330; 381/56
[58] Field of Search ............... 73/603, 570, 1 DV; 350/330; 381/56

[56] References Cited

U.S. PATENT DOCUMENTS

| | | | |
|---|---|---|---|
| 3,137,837 | 6/1964 | Wreford . | |
| 4,035,060 | 7/1977 | Tsunoda et al. | 350/332 |
| 4,338,821 | 7/1982 | Dion | 73/603 |

Primary Examiner—Howard A. Birmiel
Attorney, Agent, or Firm—Gerald S. Geren

[57] ABSTRACT

There is disclosed herein an acoustic or ultrasonic power meter which includes a liquid crystal cell for detecting acoustic energy and a control circuit for applying an electric field to said cell. The liquid crystal cell includes a liquid crystal material having elongated molecules. The preferred liquid crystal is in the form of a layer of the nematic type which is homeotropically aligned. The elongated liquid crystal molecules exhibit positive dielectric anisotropy wherein the dielectric constant parallel to the molecule's axis is greater than the dielectric constant perpendicular to the molecule's axis. In the unexcited condition, the nematic layer is dark. In the ultrasonically excited condition, the nematic layer exhibits birefringence. A restoring electric force can be applied to the liquid crystal material to suppress the acoustically-induced birefringence condition of the cell to the dark appearance associated with the unexcited condition. The strength of the electric field required to suppress the birefringence is proportional to the acoustic intensity of the ultrasonic beam or acoustic field applied to the cell.

15 Claims, 5 Drawing Figures

ACOUSTIC POWER METER

BACKGROUND OF THE INVENTION

This invention relates to an ultrasonic power meter, and more particularly, to a meter which incorporates a liquid crystal cell as an acoustic detector.

Ultrasonic inspection devices are being used in increasing numbers in industrial and medical applications. In such devices a beam of ultrasonic or acoustic energy is directed at the body to be examined and the ultrasonic energy passing through or reflected from said body is detected and visually displayed to show internal features of the body. In industrial applications such inspection techniques are usually used to detect failure-initiating internal flaws. In medical applications ultrasonics are used diagnostically to inspect internal organs, examine a fetus, and the like.

In all applications it is desirable to maintain the incident energy at the lowest effective level. It may also be desirable to measure and quantify the incident energy. In medical applications it is particularly desirable to quantify and keep the incident energy at the lowest effective level so as to avoid injuring a patient. Depending upon the application, it may also be desirable to measure or quantify the acoustic energy reflected from and/or transmitted through the body.

Meters for measuring acoustic energy are described and disclosed in U.S. Pat. No. 3,137,837, E. S. Wreford and in *Physical Principles of Ultrasonic Diagnosis* by P. N. T. Wells, Academic Press, London, England. Those references disclose the use of heat, radiation and suspended aluminum flakes to detect the ultrasonic energy incident on the measuring device. However, such devices are not in widespread commercial use. It also appears that the meter disclosed in U.S. Pat. No. 3,137,837 may have drawbacks due to the aluminum flakes used therein. For example, gravity causes the flakes to settle to the bottom of the cell and thus cause uneven and unreliable results. Furthermore, the flakes may chemically react with the suspension and chemically degrade the cell, and it is known that the response time for the aluminum flakes is poor.

It is an object of this invention to provide a device in which the detector will uniformly respond to incident acoustic energy and to an applied electric field.

It is another object to provide a meter in which the detecting medium is stable, does not chemically degrade and has an acceptable response time.

It is still another object of this invention to provide an easily used and commercially acceptable meter which can be used in industrial and medical applications.

These and other objects of the invention will become apparent from the following description and appended claims.

SUMMARY OF THE INVENTION

It has been discovered that an ultrasonic meter which includes a liquid crystal cell as the detector overcomes the disadvantages of the prior art measuring devices. The liquid crystal detector cell includes elongated liquid crystal molecules which react to both acoustic and electric fields and which have an acceptable response time. Furthermore, liquid crystal materials are now available that do not chemically degrade. Liquid crystals are dielectric and exhibit dielectric anisotropy, which means that the dielectric constant is different in the direction parallel to the molecule's longitudinal axis than in the direction perpendicular to the molecule's axis. In this particular system the dielectric constant is positive, which means that the parallel dielectric constant is greater than the perpendicular dielectric constant. Furthermore, liquid crystal molecules are not in a suspension, thus the molecules will not settle and the cell exhibits very uniform characteristics. The liquid crystal molecules are small, on the order of 20 Å in length, as compared to micrometers for the aluminum flakes, and thus provide a high resolution image.

It has also been determined that meters which use liquid crystal cells are sensitive to low levels of acoustic energy and due to cell construction can detect ultrasonic energy incident on the cell throughout a wide range of incident angles and over a range of frequencies between about 1 and 10 megahertz.

These features provide an ultrasonic power meter which can be used commercially and particularly in medical applications.

DESCRIPTION OF THE PREFERRED EMBODIMENT

Figure 1:
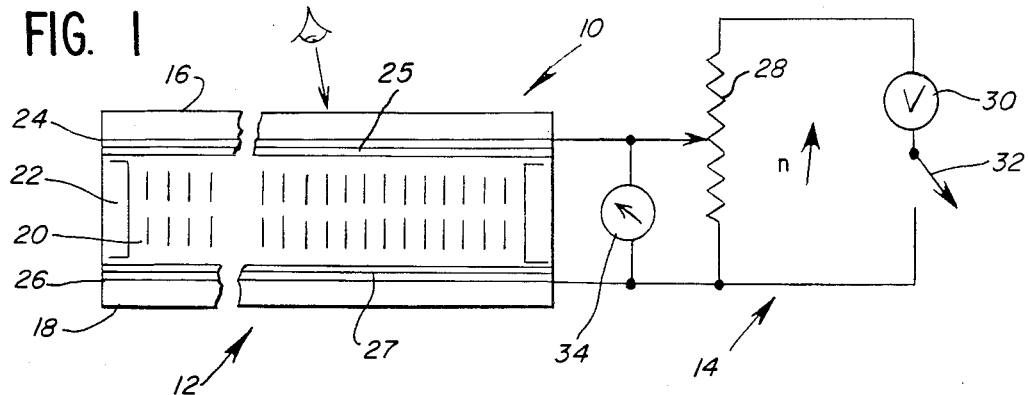
FIG. 1 is a diagrammatic cross-sectional view showing an ultrasonic power meter which includes a liquid crystal detector cell and means for applying an electric field to said cell, with the cell shown in a relaxed or unexcited state.

Referring now to FIG. 1, there is diagrammatically shown an ultrasonic power meter, or acoustic energy measuring device 10 which includes a liquid crystal detector cell 12 to which an electric field can be applied through the control circuit 14.

The cell 12 includes a pair of parallel, but closely spaced, cover plates 16 and 18, each of which is substantially acoustically transparent and at least one of which is optically transparent. The liquid crystal material 20 is positioned between the covers and sealed in place by a peripheral seal and spacer 22. The preferred liquid crystal material is of the nematic type which is homeotropically aligned. A twisted nematic which includes small amounts of cholesteric (i.e., 0.03% by weight) may also be used.

A specific liquid crystal material which is preferred is known as biphenyl and is sold under the trade identification K15 by a company known as BDH in Poole Dorset, England.

The cell covers are fabricated so that the acoustic impedence of the cover approximates the acoustic impedence of water. One such cover is a laminated glass structure in which the thickness of each glass layer is much, much less than the wavelength of the acoustic energy divided by four (i.e., $<w1/4$). U.S. patent application, Ser. No. 232,247 filed Feb. 6, 1981 discloses the details for constructing a laminated cover.

The homeotropic nematic liquid crystal is selected since in the relaxed or unexcited state the liquid crystal molecules are aligned generally normal to the cover and parallel to each other. Nematic liquid crystal molecules are elongated, dielectric and anisotropic. Dielectric anisotropy is characterized by a difference in dielectric constant in the direction parallel to and perpendicular to the molecule's longitudinal axis. The parallel constant is identified as $\epsilon_\|$, the perpendicular constant as $\epsilon_\perp$. In this meter, the parallel dielectric constant must be greater than the perpendicular constant (i.e., $\epsilon_\| > \epsilon_\perp$) or the difference in constants must be positive (i.e., $\Delta\epsilon = \epsilon_\| - \epsilon_\perp > 0$). For example, $\Delta\epsilon$ for K15 sold by BDH of Poole Dorset, is +11. When the difference in constants is positive, the liquid crystal molecules align themselves parallel to an applied electric field.

The circuit means 14 includes a pair of planar thin film electrodes 24 and 26, one of which is applied to each of the covers 16 and 18. The electrodes are preferably applied to the inside surface of the covers so as to be close to the liquid crystal material. Such thin film electrodes are prepared by vacuum deposition of Indium/tin oxide. In order to prevent chemical reaction between the electrodes and the liquid crystal material, $SiO_2$ barrier layers, such as 25 and 27, are provided. The barrier layer also prevents ion migration or a plating-like electrochemical reaction. Each of the electrodes are connected to the control circuit which includes a potentiometer 28, a voltage source 30, a switch 32, and display 34. At least one of the electrodes, such as 24, is optically transparent so as to permit the visual observation of the liquid crystal cell.

The voltage source may be DC, or may be low frequency AC. Low frequency square waves have been found to be very effective. High frequency AC should be avoided as it may cause undesired oscillation in the molecules. The display 34 may be either analog or digital. The character "$\nearrow n$" is known as a director and the arrow points in the direction in which the liquid crystal molecules are aligned on average.

In FIG. 1 the liquid crystal molecules are shown in the relaxed or unexcited state with the director normal to the cell covers. In FIG. 1 no ultrasonic or electric fields are applied to the cell. The switch 32 is open and the display 34 is at a zero (0) or null point. When the cell is viewed between crossed-polars, the cell or field of view appears dark.

Figure 2:
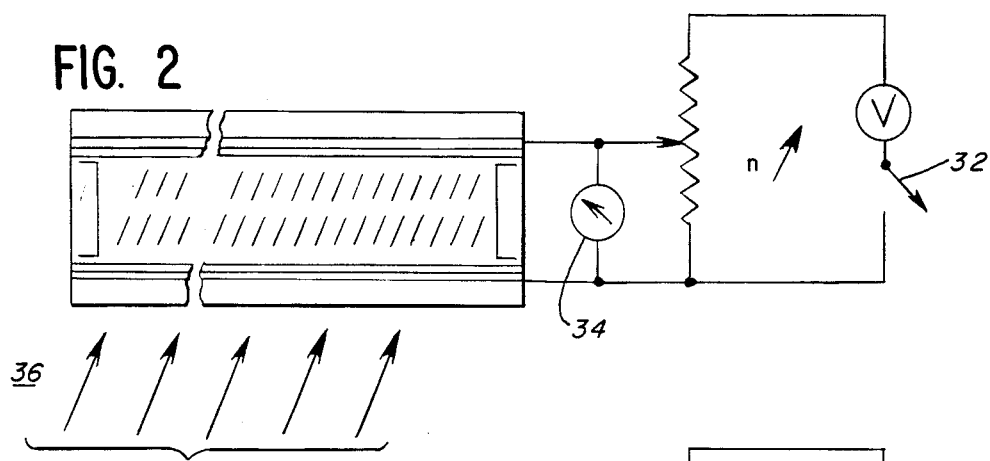
FIG. 2 is a diagrammatic view of the power meter of FIG. 1 with an ultrasonic beam incident upon the liquid crystal cell.

Referring now to FIG. 2, the cell has been placed in an acoustic field 36 (i.e., ultrasonic beam) which strikes the cell at an angle. The acoustic energy passes through the cell and the liquid crystal molecules align themselves relative to the field as shown by the director arrow. In FIG. 2 the electric field has not been applied to the cell and the display is still at zero (0). Acoustically-induced birefringence is observed.

Figure 3:
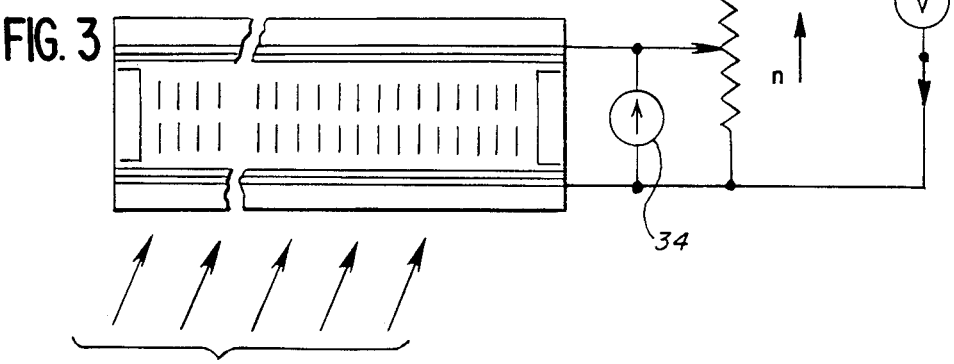
FIG. 3 is a diagrammatic view of the power meter showing an ultrasonic beam incident upon the liquid crystal cell and an electric field applied to the cell.

In order to obtain a measurement of the intensity (I) of the acoustic field, the electric field is activated by closing the switch 32 as shown in FIG. 3. The potentiometer is then adjusted until the acoustically-induced birefringence is suppressed and the cell again appears dark. When the cell exhibits a uniform dark appearance, similar to that of the unexcited state, it can be assumed that the molecules have returned to their original position as indicated by the director arrow.

As shown, the cell can be observed from at least one side and through one electrode. When it is determined that the molecules have returned to the normal position, the value indicated by the display 34 is noted. This value indicates the electrical energy, or voltage, necessary to counterbalance the acoustic intensity and restore the cell to the unexcited condition.

The meter can be calibrated so that it indicates directly the acoustic energy incident on the cell. There are thermal, electrical and mechanical techniques for calibrating the meter.

In the thermal technique incident acoustic energy is directed into a liquid, such as carbon tetrachloride ($CCl_4$) which absorbs the incident acoustic energy. The absorption will increase the liquid temperature and from the temperature change the amount of energy absorbed can be calculated. Alternatively, an electric heating element can be used to heat the $CCl_4$ to the acoustically heated temperature and the energy thus added can be determined from the expression $P = V^2/R$. By exposing the meter to the same acoustic energy level, the energy for the restoring voltage can be determined. By using several different acoustic energy levels, correlation can be established between (1) absorbed or incident acoustic energy and (2) the restoring electric force. In this way the meter can be calibrated to indicate the actual intensity of an acoustic field incident on the meter.

Figure 4:
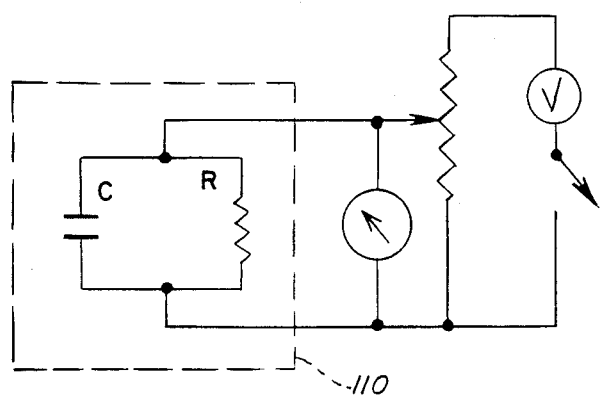
FIG. 4 is a diagrammatic analysis of the meter as part of an electric circuit.

In the electrical technique the liquid crystal cell is assumed to act as an RC element 110, as shown in FIG. 4. As previously indicated, the voltage source can be either DC or low frequency AC. In the DC case, the resistance and capacitance of the cell is known or can easily be measured, and the applied voltage is known. Using elementary DC circuit analysis, it is known that the capacitor does not consume energy, and the power or energy consumed by the resistor is defined by $I^2R$. The resistance is known and since the voltage is known, the power lost to the resistance element can be determined from the equation $P = V^2/R$. The power so determined is the electrical energy which has been added in order to counterbalance the incident acoustic energy, and thus both energies are equal. Thus, the meter can be calibrated by using sources of different acoustic energy, observing the counterbalancing voltage and calculating the related counterbalancing power. In this way the acoustic energy/restoring voltage relationship can be determined. Of course, if DC calibration is used, then the meter in actual use is provided with a DC power source.

When AC analysis is used, the reactance ($X_C$) of the capacitor can be measured and the resistance (R) for the resistor is known. The impedance (Z) of the RC element is determined from the expression:

$$1/Z = 1/R + 1/X_C$$

The total current ($I_T$) can be determined from the expression:

$$V = (I_T) Z$$

where (V) is known and (Z) has previously been determined.

In order to determine the power consumed by the resistive element (R), it is necessary to determine the current ($I_R$) at the resistor. But $$I_T = I_R + I_C$$

where $I_T$ is the total current, $I_R$ is the current through the resistor, and $I_C$ is the current at the capacitor. $I_T$ has been previously determined using $$I_T = V/Z$$

$I_C$ is determined from the expression $$V = I_C X_C$$

where V is known and $X_C$ is measured.

After $I_C$ is ascertained, $I_R$ is determined from $$I_R = I_T - I_C$$

and the power consumed is determined from $$P = (I_R)^2 R$$

Thereafter, the meter can be calibrated as disclosed in relation to the DC analysis.

Suitable AC frequencies can be between 0-50 kilohertz. Again, if AC calibration is used, the meter should be AC powered.

The energy determined by the thermal testing can be compared to the energy calculated using circuit analysis in order to verify the calibration.

Figure 5:
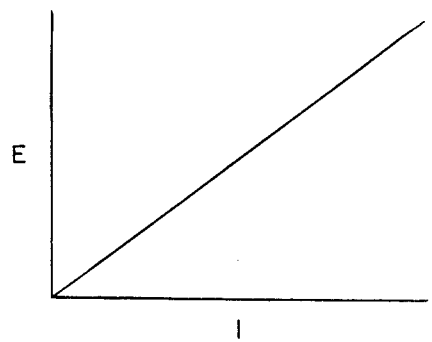
FIG. 5 is a diagram depicting the linear relationship between ultrasonic or acoustic energy and restoring electrical force.

It has been determined that there is a linear relationship between incident acoustic energy (I) and the restoring electric force (E). That relationship is shown in FIG. 5.

It has been determined that square waves provide a very suitable power source. Similar circuit analysis can be carried out to determine the power consumption across the resistor (R) when square waves are used.

In theory, the restoring electric force overcomes the mechanical forces imposed on the liquid crystal molecules due to the ultrasonic field. The electric field acts upon the molecules by virtue of the dielectric anisotropy and causes them to move to the normal or perpendicular position as indicated by the director because the parallel dielectric constant is greater than the perpendicular constant. Thus the voltage necessary to restore the cell to the unexcited condition is proportional to the strength of the ultrasonic field.

In some applications the ultrasonic transducer is coupled to the body to be inspected by a water bath. In order to ascertain the ultrasonic power incident on the body, the meter would be of a waterproof construction and inserted in the bath between the source and body.

However, in many applications it is impractical to immerse the body and the meter is coupled to the body by a film of acoustic couplant such as silicone liquid. In these situations, the entire housing need not be waterproof.

Having the ability to measure or quantify the acoustic energy will permit users to set safe operating levels, determine thresholds, determine optimum energy requirements, and the like, for various ultrasonic inspection techniques. For example, in the medical field safe levels of ultrasonic radiation for various medical procedures may be determined and regulated.

This meter has a number of advantages. For example, the distribution of acoustic energy within a field can be observed and the values associated with that distribution determined. Thus potentially dangerous "hot spots" can be observed, their values determined and danger in their use avoided. Furthermore, the birefringent effect of the liquid crystal is effectively utilized and the liquid crystals can be observed between crossed-polarizers.

It will be appreciated that numerous changes and modifications can be made to the device disclosed herein without departing from the spirit and scope of this invention.

What is claimed and desired to be secured by Letters Patent of the United States is:

1. A method of calibrating an acoustic power meter which includes a liquid crystal detector cell and circuit means for controllably applying a DC electric field to said cell, said method comprising the steps of:
   (a) determining the electrical resistance of the detector cell;
   (b) providing different levels of acoustic energy;
   (c) exposing said cell to a plurality of said different levels of acoustic energy and determining the voltage required to restore the cell to the unexcited condition for each of said levels;
   (d) determining from the resistance of the cell and voltage applied thereto the power required to restore the cell to the unexcited condition for each of said levels; and
   (e) correlating the observed voltage and determined power for each level, with the restoring power being equivalent to the incident energy.

2. A method of calibrating an acoustic power meter which includes a liquid crystal detector cell and circuit means for controllably applying an AC electric field to said cell, said method comprising the steps of:
   (a) determining the electrical impedance of the detector cell;
   (b) providing different levels of acoustic energy;
   (c) exposing said cell to a plurality of said different levels of acoustic energy and determining the voltage required to restore the cell to the unexcited condition for each of said levels;
   (d) determining from the impedance of the cell and voltage applied thereto the power required to restore the cell to the unexcited condition for each of said levels; and
   (e) correlating the observed voltage and determined power for each level, with the restoring power being equivalent to the incident energy.

3. A method for determining the actual intensity of an acoustic field using an apparatus which includes a liquid crystal detector cell that includes a pair of acoustically transparent substrates having a liquid crystal material disposed and sealed therebetween, said cell characterized by being responsive to incident acoustic energy by exhibiting birefringence means for applying a restoring electric field to said cell, said method including the steps of:

providing a cell in which the liquid crystal is in an initial condition;
   exposing said cell to an acoustic field which causes the liquid crystal to change from the initial condition to a second condition;
   applying a restoring electric field to said cell so as to suppress acoustically-induced birefringence and restore said cell to the initial condition; and
   relating the applied restoring electric field with the acoustic field so as to determine the actual intensity of the acoustic field.

4. A method as in claim 3, wherein said initial condition is an unexcited condition.

5. A method as in claim 3, wherein the applied restoring electric field is linearly related to the actual intensity of the acoustic field.

6. An apparatus for measuring the actual intensity of an acoustic field comprising:
   a liquid crystal display cell which includes a pair of acoustically transparent substrates having a liquid crystal material disposed and sealed therebetween, said liquid crystal material characterized by being responsive to incident acoustic energy by exhibiting birefringence;
   circuit means operatively associated with said cell for controllably applying a restoring electric field to said cell so as to suppress acoustically-induced birefringence; and
   means for relating the applied restoring electric field with the acoustic field so as to determine the actual intensity of the acoustic field.

7. An apparatus as in claim 6, wherein the liquid crystal material has elongated molecules, is a dielectric, exhibits dielectric anisotrophy and the dielectric constant in parallel direction is greater than the dielectric constant in the perpendicular direction.

8. An apparatus as in claim 7, wherein the liquid crystal is of the nematic type with the molecules aligned parallel to each other and substantially normal to the substrates.

9. An apparatus as in claim 6, wherein the circuit means includes a pair of electrodes, one electrode applied to each of said substrates so as to apply an electric field to liquid crystal molecules disposed between the electrodes.

10. An apparatus as in claim 9, wherein the electrodes are planar thin film members applied to the inner surfaces of the cover members.

11. An apparatus as in claim 6, wherein said circuit means includes a direct current power source.

12. An apparatus as in claim 6, wherein said circuit means includes a low frequency alternating current power source.

13. An apparatus as in claim 6, wherein said circuit means includes a square-wave generating power source.

14. An apparatus as in claim 6, wherein said circuit means for applying a restoring electric field includes means for controlling said field.

15. An apparatus as in claim 6, wherein the applied restoring electric field is linearly related to the actual intensity of the acoustic field.

* * * * *